United States Patent [19]

Tjia

[11] Patent Number: 5,143,537
[45] Date of Patent: Sep. 1, 1992

[54] CONTROL OF FLOWERING OF TROPICAL ORNAMENTALS

[75] Inventor: Benny O. Tjia, Homestead, Fla.

[73] Assignee: University of Florida Research Foundation, Inc., Gainesville, Fla.

[21] Appl. No.: 668,755

[22] Filed: Mar. 14, 1991

Related U.S. Application Data

[63] Continuation of Ser. No. 411,348, Sep. 22, 1989, abandoned, which is a continuation-in-part of Ser. No. 231,129, Aug. 11, 1988, abandoned.

[51] Int. Cl.⁵ ............................................. A01N 43/54
[52] U.S. Cl. ............................................. 71/92; 71/77; 71/90; 71/93; 71/103; 71/113; 71/114
[58] Field of Search ........................................ 71/92

[56] References Cited

PUBLICATIONS

Adriansen, "The effect of ethephon & ancymidol in F. hybrida", *Tidssps. Planteavl*, 1978, 82(3), pp. 429–32; (C.A. of . . . ).

Neel, "The Influence of A-rest upon growth and flowering of I. coccinea C.V. 'Nora Grant'", *Fl. St. Horticultural Society*, 1973, pp. 415–418.

Ho et al., "Effect of Chemicals & Photoperiod on the growth & flowering of Thanksgiving Cactus", *J. Am. Soc. Hortic. Sci.*, 1985, 110(5), pp. 658–662; (C.A. of . . . ).

Taylor, H. M., J. D. Davenport, and R. E. Hackler; U.S. Pat. No. 3,868,244; issued Feb. 25, 1975.

*Primary Examiner*—Carolyn Elmore
*Assistant Examiner*—Brian M. Burn
*Attorney, Agent, or Firm*—Saliwanchik & Saliwanchik

[57] ABSTRACT

The process of the invention provides for inducing the flowering of tropical ornamental plants at times when they do not flower naturally, by contacting the foliage with higher concentrations of a plant growth regulator. The benefits of this process are that horticulturists and landscapers can time the flowering of plants for certain times, or market demands.

6 Claims, No Drawings

CONTROL OF FLOWERING OF TROPICAL ORNAMENTALS

CROSS REFERENCE TO A RELATED APPLICATION

This application is a continuation of application Ser. No. 07/411,328, filed Sep. 22, 1989, now abandoned, which is a continuation-in-part of my copending application Ser. No. 231,129, filed Aug. 11, 1988, now abandoned.

BACKGROUND OF THE INVENTION

Tropical ornamentals are used widely as potted plants and for landscape purposes. The natural flowering habit of such plants is generally sporadic, unpredictable, and not simultaneous. It would be desirable to be able to control the flowering of tropical ornamentals, and, also, to enhance the flowering along with having multiple flowering cycles. These desired are shared by all in the tropical ornamental industry, but, unfortunately, there is no prior known art way to accomplish these laudable goals. The invention which is described herein achieves these goals in a novel and nonobvious manner.

BACKGROUND OF THE INVENTION

The subject invention concerns a novel process for inducing the flowering of tropical ornamentals at times when they do not flower naturally. More specifically, the invention concerns the use of a plant growth regulator (PGR) compound to induce the flowering of tropical ornamentals.

Exemplifying the subject invention is the use of various known PGR compounds to control the flowering of tropical ornamental at times when they do not flower naturally. For example, the application of ancymidol to the foliage of *Ioxra taiwanensis* results, after a relatively precise period of time, in full (simultaneous) flowering of the plant. The post-harvest flowering quality generally lasts for about 31 days. Upon cessation of flowering, the plant can be treated again with the PGR. After another time period simultaneous flowering will occur again.

Thus, the subject invention provides for complete control of flowering. This control allows for a better and more extended use of tropical ornamentals by the horticulture and landscape industries.

DETAILED DESCRIPTION OF THE INVENTION

Upon contacting the foliage of a tropical ornamental plant with an effective flowering inducing amount of at least one PGR, there is obtained a controlled flowering stage in a predetermined amount of time.

Any tropical ornamentals can be treated, for example, various Ixora species, such as *Ixora taiwanensis, Ixora maui* and *Ixora nor grande,* gardenias, oleanders, adenium mandevilla, Hibiscus, for example, *Hibiscus Rosa Sinensis,* and the like.

Examples of PGRs which may be used in the invention are as follows:

| Trade Name | Chemical Name | Common Name | Supplier |
|---|---|---|---|
| A-Rest | alpha-Cyclopropyl-alpha-(4-methoxyphenyl)-5-pyrimidinemethanol | Ancymidol | Eli Lilly & Company |
| B-Nine | Daminozide butanedioic acid mono(2,2-dimethylhydrazide) | Alar | Uniroyal Chemical |
| Dropp | N-phenyl-N'-1,2,3-thiadiazol-5-yl urea | Thidiazuron | Noram |
| Embark | Diethanolamine salt of (N-[2,4-dimethyl-5-[[(trifluoromethyl)sulfonyl]amino]phenyl acetamide | Mefluidide | 3M |
| Stik | 1-Naphthaleneacetic acid | NAA | Union Carbide |
| Cutless | analog of ancymidol | | Eli Lilly & Company |
| Bonzi | (±)-(R*,R*)-β-(4-Chlorophenyl)methyl)-alpha-(1,1-dimethylethyl)-1H-1,2,4-triazole-1-ethanol | Paclobutrazol | Sandoz |
| Sumagic | (E)-1-(p-chlorophenyl)-4,4-dimethyl-2-(1,2,4-triazol-1-yl)-1-penten-3-ol | Uniconizole | Chevron |
| Promuline | | Benzyladenine | Abbott Labor. |

Any analog or derivative of the above or other PGRs can be used in the invention so long as they are non-phytotoxic. Optimal concentrations of PGRs can be easily determined by those skilled in the art. Generally, such concentrations can be expected to be about 3 to 4 times, or more, the concentration of the PGR used for plant growth regulation.

The PGRs given above are examples only. Other PGRs can be used so long as they are non-phytotoxic at the concentrations necessary to induce flowering, as described herein. Presently, ancymidol is the preferred PGR. Also, the PGRs can be used in mixtures with each other.

An effective flowering inducing amount of a PGR is an amount in the range of about 3 to about 4 times or more of the amount the PGR is generally used as a plant growth regulator, This then highlights the nonobviousness of the subject invention. If the PGR is used at the level normally indicated for plant growth regulation, controlled flowering does not occur.

Following are examples which illustrate procedures, including the best mode, for practicing the invention. These examples should not be construed as limiting. All percentages are by weight and all solvent mixture proportions are by volume unless otherwise noted.

EXAMPLE 1

Control of Flowering of *Ixora taiwanensis* by Use of Ancymidol

*Ixora taiwanensis* plants were given a specific misting until runoff of a mixture consisting of water, a standard horticulturally acceptable surfactant to enhance the coverage of the PGR, and 150 mg/liter of ancymidol. When applied to the foliage of the plants, the PGR composition temporarily changes the hormonal balance within the plant system from a vegetative to the complete reproductive stage. The effect of the PGR composition is temporary, and following full bloom, plants will revert back to normal. No damage or impediment of normal growth affects the plants following the flowering period. Treated plants will develop flowers from each growing point and mature within about 75-76 days in the summer and about 120–125 days in winter. See the following Tables 1 and 2.

*Ixora taiwanensis* does not flower normally in the winter because of the cold temperatures. If they flower, they do so sporadically.

TABLE 1

Control of flowering of *Ixora taiwanesis* by the application of ancymidol at various concentrations.
(Summer - Temperature range 70° F. to 90° F.)

| Chemical Treatment | Concentration (ppm) | Days to flower | Height (cm) | # of inflorescence per plant | % flowering |
|---|---|---|---|---|---|
| Control | no chemical | sporadic | 36.0 | 3.0 | 2 |
| Ancymidol | 37.5 ppm | 76 | 29.0 | 35.4 | 90 |
| Ancymidol | 75.0 ppm | 78 | 23.8 | 40.6 | 100 |
| Ancymidol | 150.0 ppm | 78 | 24.4 | 40.4 | 100 |
| Ancymidol | 264.0 ppm | 75 | 24.2 | 40.6 | 100 |

TABLE 2

Control of flowering of *Ixora taiwanensis* by the application of ancymidol at various concentrations.
(Winter - Temperature range 60° F. to 75° F.)

| Chemical Treatment | Concentration (ppm) | Days to flower | Height (cm) | # of inflorescence per plant | % flowering |
|---|---|---|---|---|---|
| Control | no chemical | — | | 0 | 0 |
| Ancymidol | 18.8 ppm | — | | 2 | 6 |
| Ancymidol | 37.5 ppm | — | | 10 | 47 |
| Ancymidol | 75.0 ppm | 123 | | 46 | 100 |
| Ancymidol | 150.0 ppm | 122 | | 53 | 100 |

The critical ingredient is the PGR in the above tests. The surfactant, as noted above, is merely used to enhance coverage. Surfactants which can be used include anionic, cationic, and non-ionic agents. See "Detergents and Emulsifiers" 1971 Annual by John W. McCutcheion, Inc., for a disclosure of surfactants. Generally, 1–10% by weight of the surfactant can be used. Specific adjustments can be made by persons skilled in the art using routine procedures.

The PGR can be formulated into standard well-known formulations for horticultural and landscape uses, as well as for home owners. It can be marketed in concentrations suitable for inducing the flowering of tropical ornamentals.

EXAMPLE 2

Control of Flowering of Hibiscus Rosa Sinensis by the Application of Growth Regulator Paclobutrazol at Various Concentrations. Winter 1988 (October–December), 1989 (January–February)*

*Hibiscus at this time usually do not flower due to prevailing cold temperatures in South Florida. If they flower, they do so sporadically.

| Treatment | Concentration mg (pot) | Total number of flowers per plant | Height (cm) | Number of inflorescence per stem |
|---|---|---|---|---|
| Control | No chemical | 0 | 99.5 | 0 |
| Paclobutrazol | 6 mg | 5.0 | 66.6 | each node has flowers |
| Paclobutrazol | 18 mg | 10.5 | 45.5 | each node has flowers |

EXAMPLE 3

Induction of Flowering of *Ixora taiwanensis* by the Application of Various Growth Regulators at Various Concentrations (Jan. 1988)

| Chemical treatment | Concentration (ppm) | Days to flower | Height (cm) | Number of flowers | % flowering |
|---|---|---|---|---|---|
| Control | — | — | 31.8 | 0 | 0 |
| Ancymidol | 18.8 | 124 | 29.8 | 8.6 | 17.9 |
| | 37.5 | 123 | 30.8 | 18.4 | 38.3 |
| | 75.0 | 120 | 26.0 | 36.6 | 76.1 |
| | 150.0 | 119 | 26.0 | 49.8 | 100.0 |
| Paclobutrazol | 100.0 | 122 | 24.2 | 38.8 | 100.0 |
| | 200.0 | 120 | 23.8 | 47.6 | 100.0 |
| Uniconizole | 25.0 | 118 | 23.6 | 47.8 | 100.0 |
| | 50.0 | 119 | 25.8 | 47.2 | 100.0 |

EXAMPLE 4

Induction of Flowering of *Ixora taiwanensis* by the Application of Various Growth Regulator Mixes (May 1988)

| Treatment (ppm) | Number of flowers | % flowering | % Bypass shoots |
|---|---|---|---|
| Control | 0 | 0 | 0 |
| Control (ancymidol) | 29.4 | 100 | 3.4 |
| Ancymidol (100) + uniconizole (5) | 31.0 | 100 | 1.3 |
| Ancymidol (100) + uniconizole (10) | 31.6 | 100 | 0 |
| Ancymidol (150) + uniconizole (5) | 32.0 | 100 | 0 |
| Ancymidol (150) + uniconizole (10) | 32.0 | 100 | 0 |

I claim:

1. A process for inducing the flowering of Ixora at a time of the year when the prevailing high temperatures are from about 75° F. to about 90° F., comprising applying an effective amount of ancymidal about 75 to about 80 days before flowering is desired.

2. The process of claim 1, wherein said ancymidol is applied to the foliage of an Ixora.

3. The process of claim 2, wherein said Ixora is an *Ixora taiwanensis*.

4. A process for controlling the timing of flowering of Ixora at time of the year when the prevailing high temperatures are from about 60° F. to about 75° F., comprising applying an effective amount of ancymidal about 120 to about 125 days before flowering is desired.

5. The process of claim 4, wherein said ancymidol is applied to the foliage of an Ixora.

6. The process of claim 5, wherein said Ixora is an *Ixora taiwanensis*.

* * * * *

UNITED STATES PATENT AND TRADEMARK OFFICE
CERTIFICATE OF CORRECTION

PATENT NO. : 5,143,537

DATED : September 1, 1992

INVENTOR(S) : Benny O. Tjia

It is certified that error appears in the above-identified patent and that said Letters Patent is hereby corrected as shown below:

Column 1: line 20: "desired" should read --desires--; line 22: "prior known" should read --known prior--; line 36: "ornamental" should read --ornamentals--; line 58: "nor grande" should read --nora grande--.

Column 2: line 42: "regulator, This" should read --regulator. This--.

Column 4: line 50 (claim 1): "ancymidal" should read --ancymidol--; line 57 (claim 4): "at time" should read --at a time--; line 59 (claim 4): "ancymidal" should read --ancymidol--.

Signed and Sealed this

Fourteenth Day of September, 1993

Attest:

BRUCE LEHMAN

Attesting Officer　　　Commissioner of Patents and Trademarks